US010759773B2

(12) United States Patent
Gibanel et al.

(10) Patent No.: US 10,759,773 B2
(45) Date of Patent: Sep. 1, 2020

(54) POLYCYCLOCARBONATE COMPOUNDS AND POLYMERS FORMED THEREFROM

(71) Applicant: SWIMC LLC, Cleveland, OH (US)

(72) Inventors: Sebastien Gibanel, Givry (FR); Benoit Prouvost, L'Abergement de Cuisery (FR)

(73) Assignee: SWIMC LLC, Cleveland, OH (US)

( * ) Notice: Subject to any disclaimer, the term of this patent is extended or adjusted under 35 U.S.C. 154(b) by 37 days.

(21) Appl. No.: 15/991,545

(22) Filed: May 29, 2018

(65) Prior Publication Data

US 2018/0273502 A1 Sep. 27, 2018

Related U.S. Application Data

(63) Continuation of application No. 15/299,532, filed on Oct. 21, 2016, now Pat. No. 10,000,461, which is a continuation of application No. PCT/US2015/027438, filed on Apr. 24, 2015.

(60) Provisional application No. 61/984,523, filed on Apr. 25, 2014.

(51) Int. Cl.
*C08G 63/58* (2006.01)
*C08G 65/38* (2006.01)
*C07D 317/36* (2006.01)
*C09D 171/10* (2006.01)
*C08G 65/40* (2006.01)
*C09D 171/00* (2006.01)

(52) U.S. Cl.
CPC ............ *C07D 317/36* (2013.01); *C08G 65/38* (2013.01); *C08G 65/4043* (2013.01); *C09D 171/00* (2013.01); *C09D 171/10* (2013.01)

(58) Field of Classification Search
None
See application file for complete search history.

(56) References Cited

U.S. PATENT DOCUMENTS

| | | | |
|---|---|---|---|
| 2,448,767 | A | 9/1948 | Carlson et al. |
| 2,967,892 | A | 1/1961 | Smith |
| 2,987,555 | A | 6/1961 | Davis |
| 4,261,922 | A | 4/1981 | Kem |
| 4,341,905 | A | 7/1982 | Strege |
| 4,348,314 | A | 9/1982 | Lazarus et al. |
| 5,059,723 | A | 10/1991 | Dressler |
| 5,431,791 | A | 7/1995 | December et al. |
| 5,665,433 | A | 9/1997 | Moussa et al. |
| 5,714,568 | A | 2/1998 | Nava |
| 5,994,469 | A | 11/1999 | December |
| 8,129,495 | B2 | 3/2012 | Evans et al. |
| 8,633,327 | B2 | 1/2014 | Guylas et al. |
| 8,741,988 | B2 | 6/2014 | Klopsch |
| 2009/0036645 | A1 | 2/2009 | Stopek |
| 2009/0208553 | A1 | 8/2009 | Kemp et al. |
| 2012/0215020 | A1 | 8/2012 | Raether et al. |
| 2012/0215030 | A1 | 8/2012 | Raether |
| 2012/0264941 | A1 | 10/2012 | Jerome et al. |
| 2013/0206756 | A1 | 8/2013 | Niederst et al. |
| 2013/0316109 | A1 | 11/2013 | Niederst et al. |
| 2013/0323491 | A1* | 12/2013 | Takahashi ............ C09D 175/12 428/220 |
| 2014/0191156 | A1 | 7/2014 | Marks et al. |
| 2015/0021323 | A1 | 1/2015 | Niederst et al. |
| 2015/0110981 | A1 | 4/2015 | Dudik et al. |
| 2017/0096579 | A1 | 4/2017 | Gibanel |

FOREIGN PATENT DOCUMENTS

| | | | |
|---|---|---|---|
| CA | 1303051 C | 6/1992 | |
| CN | 1175288 A | 3/1998 | |
| CN | 104559681 A * | 4/2015 | |
| CN | 104559681 A | 4/2015 | |
| EP | 1020457 A1 | 7/2000 | |
| JP | 2012236925 A | 12/2012 | |
| WO | 2007055929 A1 | 5/2007 | |
| WO | 2011061452 A2 | 5/2011 | |
| WO | WO-2011061452 A2 * | 5/2011 | ............ C07D 317/36 |
| WO | 2013028292 A1 | 2/2013 | |
| WO | 2013093346 A1 | 6/2013 | |
| WO | 2013119686 A1 | 8/2013 | |
| WO | 2015164703 A1 | 10/2015 | |

OTHER PUBLICATIONS

Computer-generated English-language translation of CN-104559681-A.*
Toullec et al., Tetrahedron Letters 41 (2000) 5527-5531.*
Extended Search European Search Report for Application No. EP157833427, dated Mar. 3, 2018, Munich.
Gabriel Rokicki, Jerzy Pawlicki, & Witold Kuran, "Poly(ethercarbonate)s from Diphenolates, Cyclic Carbonates, and Dihalo Compounds", Polymer Journal, Jun. 13, 1984, pp. 509-516, vol. 17, No. 3, Warsaw, Koszykowa 75, Poland.
Benjamin Schaffner, Matthis Blug, Daniela Kruse, Mykola Polyakov, Angela Kockritz, Andreas Martin, Prasanna Rajagopalan, Ursula Bentrup, Angelika Bruckner, Sebastian Jung, David Agar, Bettina Rungeler, Andreas Pfennig, Karsten Muller, Wolfgang Arlt, Benjamin Woldt, Michael Grab, & Stefan Bucholtz, "Synthesis and Application of Carbonated Fatty Acid Esters from Carbon Dioxide Including a Life Cycle Analysis", ChemSusChem, Mar. 11, 2014, pp. 1133-1139, vol. 10.1002, Wiley Online Library, Weinheim, Germany.
Jens Langanke, Lasse Greiner, & Walter Leitner, "Substrate Dependent Synergetic and Antagonistic Interaction of Ammonium Halide and Polyoxometalate Catalysts in the Synthesis of Cyclic Carbonates from Oleochemical Epoxides and CO2", Green Chemistry, Feb. 11, 2013, pp. 1173-1182, vol. 15, RCS Publishing.

(Continued)

*Primary Examiner* — Vu A Nguyen
(74) *Attorney, Agent, or Firm* — Honigman LLP

(57) ABSTRACT

Polycyclocarbonate compounds and upgraded molecular weight polymers made from such compounds are provided. The polymers have particular utility in coating compositions, especially for use on food and beverage contact substrates that are formed into or will be formed into containers or container components.

20 Claims, No Drawings

(56) References Cited

OTHER PUBLICATIONS

Patrik Toullec, Aranzazu Carbayo Martin, Monica Gio-Batta, Christian Bruneau, & Pierre Dixneuf, "Stereoselective Preparation of Z-Trisubstituted Alkylidene Cyclic Carbonates via Palladium-Catalysed-Carbon Bond Formation", Pergamon, Jun. 1, 2000, pp. 5527-5531, vol. 41, Tetrahedron Letters, Rennes, France.

Supplementary Partial Search European Search Report for Application No. EP15783342, dated Sep. 29, 2017, Munich.

"Synthesis of glycerin carbonate-based intermediates using thiol-ene chemistry and isocyanate free polyhyroxyurethanes therefrom," Benyahya et al, Polymer Chemistry, 2011, 2, 2661.

International Search Report and Written Opinion for International Application No. PCT/US2015/027438, dated Aug. 4, 2015, 10 pages.

"Cyclic limonene dicarbonate as a new monomer for non-isocyanate oligo- and polyurethanes (NIPU) based upon terpenes." BAHR, et al. Green Chemistry, 2012, 14, 1447. 8 pages.

"Enantioselective Addition of 2-Methyl-3-butyn-2-ol to Aldehydes: Preparation of 3-Hydroxy-1-butynes," Boyall et al. Organic Letters, 2000, vol. 2, No. 26, 4233-4236. 4 pages.

"Reactive Applications of Cyclic Alkylene Carbonates," John H. Clements, American Chemical Society, Jan. 15, 2003. (12 pages).

"Carbonates for Non-Isocyanate Polyurethane," Q. Zheng et al., Specific Polymers, 2011, 6517-6527 (3 pages).

"Renewable polymides and plyurethanes derived from limonene," Firdaus et al, Green Chemistry, 2013, 15, *370-380. (12 pages).

Technical Bulletin, "Jeffsol Alkylene Carbonates, Synthesis of Hydroxyalkyl Urethanes," Huntsman Corporation, 2005. (4 pages).

"Carboxylative cyclization of propargylamines with supercritical carbon dioxide," Yoshihito Kayaki et al. Green Chemistry, 2006, 8, 1019-1021 (3 pages).

"Five-membered Cyclic Carbonates in the Synthesis of Tetramethacrylate Monomers with Low Oxygen Inhibition," Rokicki et al., Proceeding of the World Polymer Congress, Macro 2006, 41st International Symposium on Macromolecules. (2 pages).

"Hyperbranched Aliphatic Polyethers Obtained From Environmentally Benign Monomer: Glycerol Carbonate," Rokicki et al., The Royal Society of Chemistry 2005, Green Chemistry, 20015, 7, 529-539. (11 pages).

\* cited by examiner

POLYCYCLOCARBONATE COMPOUNDS AND POLYMERS FORMED THEREFROM

CROSS-REFERENCE TO RELATED APPLICATION(S)

This application is a continuation of U.S. Non-Provisional Application No. 15/299,532, filed on Oct. 21, 2016, which is a continuation of International Application No. PCT/US2015/027438, filed on Apr. 24, 2015 and entitled "Polycyclocarbonate Compounds And Polymers Formed Therefrom," which claims the benefit of U.S. Provisional Application No. 61/984,523, filed on Apr. 25, 2014 and entitled "Polycyclocarbonate Compounds And Polymers Formed Therefrom," each of which is incorporated herein by reference in its entirety.

TECHNICAL FIELD

This invention relates to polycyclocarbonate compounds and to polymers made from them.

BACKGROUND

The application of coatings to metals to retard or inhibit corrosion is well established. This is particularly true in the area of packaging containers such as metal food and beverage cans. Coatings are typically applied to the interior of such containers to prevent the contents from contacting the metal of the container. Contact between the metal and the packaged product can lead to corrosion of the metal container, which can contaminate the packaged product. This is particularly true when the contents of the container are chemically aggressive in nature. Protective coatings are also applied to the interior of food and beverage containers to prevent corrosion in the headspace of the container between the fill line of the food product and the container lid.

Packaging coatings should preferably be capable of high-speed application to the substrate and provide the necessary properties when hardened to perform in this demanding end use. For example, the coating should be safe for food contact, not adversely affect the taste of the packaged food or beverage product, have excellent adhesion to the substrate, resist staining and other coating defects such as "popping," "blushing" and/or "blistering," and resist degradation over long periods of time, even when exposed to harsh environments. In addition, the coating should generally be capable of maintaining suitable film integrity during container fabrication and use and be capable of withstanding the processing conditions that the container may be subjected to during product packaging.

Various coatings have been used as interior protective can coatings, including polyvinyl-chloride-based coatings and epoxy-based coatings incorporating bisphenol A ("BPA"). Each of these coating types, however, has potential shortcomings. For example, the recycling of materials containing polyvinyl chloride or related halide-containing vinyl polymers can be problematic. There is also a desire by some to reduce or eliminate certain BPA-based compounds commonly used to formulate food-contact epoxy coatings.

What is needed in the marketplace is an improved binder system for use in coatings such as, for example, packaging coatings.

SUMMARY

In one aspect, the present disclosure is directed to polycyclocarbonate compounds (hereinafter "PCC" compound or compounds) useful in forming polymers, which may have utility in various end uses including, for example, coating end uses such as packaging coating end uses. The PCC compounds preferably include at least two carbonate-containing rings having a carbonate linkage (—O—C(=O)—O—) present in the ring. The carbonate-containing rings are preferably 5-member rings. In preferred embodiments, the PCC compound is a dicyclocarbonate compound. The PCC compound can be saturated or unsaturated.

In preferred embodiments, the PCC compound has the below Formula I structure:

Formula I $$(R^3)_t\!-\!\!C \underset{(R^4)_s\ R^1}{\overset{\displaystyle O}{\underset{\displaystyle O}{\bigcirc}}}\!\!(R^2)_n\!\!\underset{R^1\ (R^4)_s}{\overset{\displaystyle O}{\underset{\displaystyle O}{\bigcirc}}}\!\!C\!-\!(R^3)_t$$

wherein
  each $R^1$ is independently an atom or group, more preferably a hydrogen atom or organic group,
  $R^2$, if present, is a divalent group, more preferably a divalent organic group that preferably contains from 1 to about 50, from 1 to about 20, from 1 to about 10, or from 1 to 6 carbon atoms;
  each $R^3$ is independently an atom or group, more preferably hydrogen or an organic group, and even more preferably hydrogen,
  each $R^4$, if present, is independently an atom or group, more preferably a hydrogen or organic group,
  n is 0 or 1, more preferably 1;
  each s is independently 0 or 1, and wherein when s is 0 a double bond is located between the carbon atom to which $R^3$ is attached and the adjacent carbon atom of the carbonate-containing ring, and whereas when s is 1 a single bond is present between these two carbon atoms;
  each t is independently 1, 2, or 3, more typically 2; and
  two or more $R^1$, $R^2$ and/or $R^4$ can optionally join to form a cyclic group.

When $R^1$, $R^2$, $R^3$, and/or $R^4$ is independently an organic group, the organic group may optionally include one or more heteroatoms (e.g., S, O, N, P, etc.).

Each $R^3$ is independently attached to the depicted carbon atom in Formula (I) by a single, double, or triple bond, more typically a single bond, depending on the value of t and whether the depicted carbon atom is attached to the cyclocarbonate ring by a single or double bond. Thus, for example, if the depicted carbon atom is attached by a double bond to the cyclocarbonate ring, then t can be 1 or 2, wherein a double bond attaches a single $R^3$ to the depicted carbon atom when t is 1 and single bonds attach each of a pair of $R^3$ to the carbon atom when t is 2. When the depicted carbon atom is attached to the cyclocarbonate ring by a single bond, then one to three $R^3$ can be attached by any suitable combination of single, double, or triple bonds.

Although the PCC compound of Formula I can be of any suitable size, it will typically have a number average molecular weight (Mn) of less than about 1,500, less than about 1,000, or less than about 500.

In another aspect, the present disclosure provides a method for making PCC compounds. The method includes reacting ingredients including a first compound having carbonyl groups and a second compound having a carbon-carbon triple bond. The first and second compounds are preferably reacted to form an adduct that is further reacted with a suitable compound such as carbon dioxide to form the PCC compound. In preferred embodiments, the first compound includes at least two carbonyl functional groups, which are preferably selected from aldehyde or ketone groups. The resulting PCC compound is preferably a polycyclocarbonate compound, and more preferably a dicyclocarbonate compound which may be of the structure of Formula I.

In another aspect, the present disclosure is directed to coating compositions that include a polymer formed from ingredients including the PCC compound. In some embodiments, the polymer is a polyether polymer, and more preferably a polyether polymer that was formed without using any oxirane-functional reactants.

Preferred polymers of the present invention are suitable for use in a variety of end uses, including as a film-forming material of a coating. In some such embodiments, the polymer has a glass transition temperature ("Tg") of at least 40° C., more preferably at least 60° C., and a number average molecular weight of at least 1,000 or at least 2,000. In some embodiments, aryl or heteroaryl groups preferably constitute at least 25 weight percent of the polymer.

In yet another aspect, the present disclosure is directed to coated articles that include at least one surface having a coating formed from the coating composition of the present disclosure disposed thereon. In some embodiments, the coated articles are articles for packaging products such as, for example, food or beverage containers or portions thereof. In some embodiments, the coating composition is disposed on the interior of such containers as a food-contact coating.

In yet another aspect, the present disclosure is directed to a method for coating a substrate such as, for example, a metal substrate. In some embodiments, the method includes applying the coating composition (e.g., a liquid or powder coating composition) of the present disclosure to a substrate prior to or after forming the substrate into an article such as a packaging article (e.g., a container such as a metal food or beverage container) or a portion thereof.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Unless otherwise indicated, the structural representations included herein are not intended to indicate any particular stereochemistry and are intended to encompass all stereoisomers.

Definitions

As used herein, "a," "an," "the," "at least one," and "one or more" are used interchangeably. Thus, for example, a coating composition that comprises "a" polyether can be interpreted to mean that the coating composition includes "one or more" polyethers.

The terms "comprises" and variations thereof do not have a limiting meaning where these terms appear in the description and claims.

The term "crosslinker" refers to a molecule capable of forming a covalent linkage between copolymers (e.g., between polymers) or between two different regions of the same copolymer.

The terms "estrogenic activity" or "estrogenic agonist activity" refer to the ability of a compound to mimic hormone-like activity through interaction with an endogenous estrogen receptor, typically an endogenous human estrogen receptor.

The term "mobile" when used with respect to a compound in a coating composition means that the compound can be extracted from the coating composition when a coating (typically ~1 mg/cm$^2$) is exposed to a test medium for some defined set of conditions, depending on the end use. An example of these testing conditions is exposure of the cured coating to HPLC-grade acetonitrile for 24 hours at 25° C.

The term "on," when used in the context of a coating applied on a surface or substrate, includes both coatings applied directly or indirectly to the surface or substrate. Thus for example, a coating applied to a primer layer overlying a substrate constitutes a coating applied on the substrate.

The term "organic group" means a hydrocarbon group (with optional elements other than carbon and hydrogen, such as oxygen, nitrogen, sulfur, and silicon) that may be further classified as an aliphatic group, cyclic group (e.g., aromatic and cycloaliphatic groups), or combination of aliphatic and cyclic groups (e.g., alkaryl and aralkyl groups). The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group (e.g., an n-propyl isopropyl group). The term "alkenyl group" means an unsaturated, linear or branched hydrocarbon group with one or more carbon-carbon double bonds (e.g., a vinyl group). The term "cyclic group" means a closed ring hydrocarbon group that is classified as an alicyclic group or an aromatic group, both of which can include heteroatoms. The term "alicyclic group" means a cyclic hydrocarbon group having properties resembling those of aliphatic groups. A group that may be the same as or different from other groups may be referred to as being "independently" something. Substitution on the organic groups of compounds of the present invention is contemplated. The terms "group" and "moiety" may be used to differentiate between chemical species that allow for substitution or that may be substituted and those that do not allow or may not be so substituted. The term "group" is intended to be a recitation of both the particular moiety, as well as a recitation of the broader class of substituted and unsubstituted structures that includes the moiety. Thus, when the term "group" is used to describe a chemical substituent, the described chemical material includes the unsubstituted group (e.g., the moiety) and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, isopropyl, t-butyl, heptyl, dodecyl, octadecyl, amyl, 2-ethylhexyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, isopropyl, t-butyl, heptyl, dodecyl, octadecyl, amyl, 2-ethylhexyl, and the like.

The term "unsaturated" when used in the context of a compound refers to a compound that includes at least one non-aromatic (e.g., aliphatic) carbon-carbon double or triple bond.

The term "phenylene" as used herein refers to a six-carbon atom aryl ring (e.g., as in a benzene group) that can have any substituent groups (including, e.g., hydrogen atoms, halogen atoms, hydrocarbon groups, oxygen atoms, hydroxyl groups, etc.). Thus, for example, the following aryl groups are each phenylene rings: —$C_6H_4$—, —$C_6H_3(CH_3)$—, and —$C_6H(CH_3)_2Cl$—. In addition, for example, each of the aryl rings of a naphthalene group are phenylene rings.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "substantially free" when used with respect to a coating composition that may contain a particular mobile compound means that the coating composition contains less than 1,000 parts per million (ppm) of the recited mobile compound. The term "essentially free" when used with respect to a coating composition that may contain a particular mobile compound means that the coating composition contains less than 100 parts per million (ppm) of the recited mobile compound. The term "essentially completely free" when used with respect to a coating composition that may contain a particular mobile compound means that the coating composition contains less than 5 parts per million (ppm) of the recited mobile compound. The term "completely free" when used with respect to a coating composition that may contain a particular mobile compound means that the coating composition contains less than 20 parts per billion (ppb) of the recited mobile compound. If the aforementioned phrases are used without the term "mobile" (e.g., "substantially free of BPA compound") then the compositions of the present invention contain less than the aforementioned amount of the compound whether the compound is mobile in the coating or bound to a constituent of the coating.

Unless otherwise indicated, the term "polymer" includes both homopolymers and copolymers (e.g., polymers of two or more different monomers). Similarly, unless otherwise indicated, the use of a term designating a polymer class such as, for example, "polyether" is intended to include both homopolymers and copolymers (e.g., polyether-ester copolymers).

Also herein, the recitations of numerical ranges by endpoints include all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 4 to 5, etc.).

DETAILED DESCRIPTION

A variety of compounds may be used to prepare the disclosed PCC compounds. In certain preferred embodiments, the PCC compound is formed by reacting a first compound having carbonyl groups, with a second compound having a carbon-carbon triple bond to form an intermediate adduct (e.g., a propargylic-type alcohol such as depicted below), which is then converted into the PCC compound using one or more additional reaction steps. For example, in some embodiments, the intermediate adduct is preferably reacted with a suitable carbonation compound, which is preferably carbon dioxide, to form the PCC compound. While not intending to be bound by any theory, in some embodiments, it is believed the adduct of the first and second compounds includes pendant groups containing carbon-carbon triple bonds and that reaction of the intermediate adduct with, for example, carbon dioxide results in the formation of cyclocarbonate groups having a pendant group attached to the carbonate-containing ring via a carbon-carbon double bond. This reaction scheme is illustrated below for a generic diketone as the first compound and acetylene as the second compound.

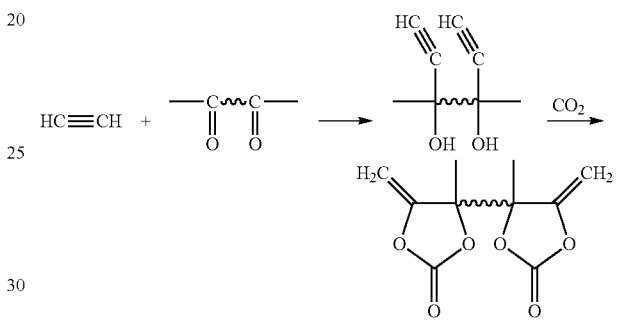

The carbonyl functional groups of the first compound are preferably selected from carbonyl groups other than carboxylic acid or ester groups. More preferably, the carbonyl groups are selected from ketone or aldehyde groups. Preferred first compounds include polyketone and polyaldehyde compounds, with diketone compounds, dialdehyde compounds, and compounds including both a single aldehyde group and a single ketone group being particularly preferred. It is contemplated that the polyketone or polyaldehyde compounds may optionally include additional carbonyl groups other than ketone or aldehyde carbonyl groups.

The first compound may be of the below Formula II structure:

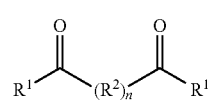

Formula II wherein
  each $R^1$ is independently an atom or group, with the proviso that the two $R^1$ groups can join to form a cyclic group;
  $R^2$, if present, is a divalent group, more preferably a divalent organic group; and
  n is 0 or 1, more preferably 1.

In preferred embodiments, $R^1$ and $R^2$ can be any suitable atom or group. Suitable such atoms or groups preferably do not react with a ketone or aldehyde group or a carbon-carbon triple bond at a temperature of less than 150° C.

In preferred embodiments, $R^1$ is a hydrogen atom or an organic group that may optionally include one or more heteroatoms (e.g., O, N, S, P, a halogen atom). Exemplary organic groups include those containing from 1 to about 50, from 1 to about 20, from 1 to about 10, or from 1 to 6 carbon atoms. In some embodiments, the organic groups are alkyl groups. One or both $R^1$ groups can include one or more cyclic groups. Examples of cyclic groups include aryl or heteroaryl groups, saturated or unsaturated cycloaliphatic groups, or combinations thereof. The cyclic groups can be monocyclic or polycyclic groups (e.g., bicyclic groups, tricyclic groups, etc.).

In preferred embodiments, $R^2$ is present and preferably constitutes a divalent organic group, more preferably a divalent organic that contains from 1 to about 50, from 1 to about 20, from 1 to about 10, or from 1 to 6 carbon atoms. In some embodiments, $R^2$ may include one or more atoms that is not C or H such as, for example, O, N, S, P, a halogen atom, or a combination thereof.

Although not presently preferred, it is contemplated that $R^1$ and/or $R^2$ may be a group that does not contain a carbon atom such as, for example, carbon-free embodiments of the following types of groups: sulfur-containing groups, nitrogen-containing groups, phosphorus containing groups, oxygen-containing groups, or silicon containing groups.

In some embodiments, $R^2$ includes one or more cyclic groups, which may be either monocyclic or polycyclic and saturated, unsaturated, or aromatic. Suitable such cyclic groups include aryl or heteroaryl group (e.g., phenylene groups) and saturated or unsaturated cycloaliphatic groups (e.g., substituted or unsubstituted cyclobutane, cyclopentane, cyclohexane, and tricyclodecane groups). Examples of polycyclic groups include saturated or unsaturated bicyclic or tricyclic or higher groups such as substituted or unsubstituted norbornane, norbornene, isosorbide, or tricyclodecane groups.

The first compound can have any suitable molecular weight, but will typically have a number average molecular weight ("$M_n$") of less than about 1,000, less than about 500, less than about 400, less than about 300, less than about 200, or less than about 150 Daltons. Exemplary first compounds include acetylacetone, glutaraldehyde, diacetylbenzene (e.g., 1,2-, 1,3-, or 1,4-diacetylbenzene), 2,6-pyridinedicarboxaldehyde, phthaldialdehyde, terephthaldehyde, isophthalaldehyde, 2-methyl-1,3-diphenylpropane-1,3-dione, 1,3-diphenyl-1,3-propanedione, 1-phenyl-1,3-butanedione, and combinations or variants (e.g., isomers or substituted variants of the listed material) thereof.

The second compound may be of the below Formula III structure:

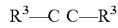    Formula III wherein each $R^3$ is independently an atom or group, more preferably hydrogen or an organic group, with the proviso that at least one $R^3$ is preferably hydrogen. In some embodiments, $R^3$ can be an organic or sulfur-containing group, oxygen-containing group, nitrogen-containing group, phosphorus-containing group, or combination thereof. Exemplary organic groups include those containing from 1 to about 50, from 1 to about 20, from 1 to about 10, or from 1 to 6 carbon atoms. In some embodiments, $R^3$ can include an aryl or heteroaryl group. In some embodiments, both $R^3$ are hydrogen atoms.

The second compound can have any suitable molecular weight, but will typically have a number average molecular weight of less than about 1,000, less than about 500, less than about 400, less than about 300, less than about 200, or less than about 100 Daltons. Examples of suitable second compounds include alkynes, and especially alkynes having a terminal carbon-carbon triple bond, such as acetylene, phenylacetylene, cyclopentylacetylene, cyclohexylacetylene, cyclopropylacetylene, 1-ethynylcyclohexene, 4-ethynyltoluene, 4-ethynylanisole, 1-butyne, 3-methyle-1-butyne, 3,3-dimethyl-1-butyne, 4-phenyl-1-butyne, 2-methyl-1-buten-3-yne, propyene, 3-phenyl-1-propyne, 1-pentyne, 5-phenyl-1-pentyne, 1-hexyne, 3-methyl-1-hexyne, 5-methyl-1-hexyne, 1-heptyne, 1-octyne, 1-decyne, and mixtures and variants thereof (e.g., isomers and substituted variants of the listed material). Acetylene is a preferred second compound in some embodiments.

In some embodiments, one or both of the first and second compounds are free of halogen atoms.

As discussed above, the first and second compounds are preferably reacted with one another to form an adduct that is preferably further reacted with a suitable carbonation compound such as carbon dioxide to form the PCC compound. In preferred embodiments, the first compound includes two carbonyl functional groups, which are preferably selected from aldehyde or ketone groups, and the resulting PCC compound is a dicarbonate compound. This reaction is believed to result in the formation of a PCC compound of the above Formula I in which s is 0, t is 2, and each depicted 5-member cyclocarbonate ring includes a $=C(R^3)_t$ group attached thereto. A PCC compound of this structure is depicted in the below Formula IV structure.

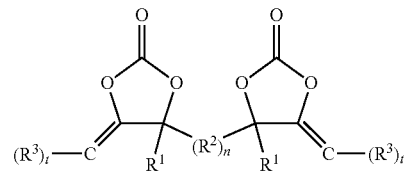

Formula IV

If desired, the carbon-carbon double bonds of the above structure of Formula IV may be consumed, e.g., in a hydrogenation reaction, in which case s of Formula I will become 1 and $R^4$ of Formula I will typically be a hydrogen atom.

Reactions to prepare the disclosed PCC compounds may be performed using a variety of temperature and pressure conditions and a variety of types of equipment. The chosen conditions may be based on a variety of factors including the chosen starting materials, the desired end use for the product and the available reaction vessel or vacuum stripping equipment. The reactions generally will be performed using appropriate stoichiometric amounts of each reactant, for example about a 2:1 ratio of first compound to second compound, with wider ranges (for example, about 10:1 to 0.01:1) being useful in some circumstances. In general, the ratio will be linked to the case of elimination of one of the compounds after reaction. The resulting PCC compounds may, for example, have a Mn of up to about 3,000, up to about 2,000, up to about 1,200, up to about 800, or up to about 600 Daltons as evaluated, for example, using gel permeation chromatography and a polystyrene standard.

One or more catalysts preferably are employed to assist in converting the starting materials to the disclosed PCC compounds. Exemplary catalysts for use in facilitating the carbonation reaction include metallic catalysts (e.g., silver acetate), quaternary ammonium salts such as, e.g., 1,3-bis (2,6-disopropylphenyl)-imidazolidinium chloride (CAS 258278-25-0), and mixtures thereof. A catalyst may also be used (e.g., a basic catalyst such as a metal hydroxide like sodium hydroxide or lithium hydroxide or a metal alcoholate like sodium methylate), for example, to facilitate reaction of the first and second compounds prior to carbonation of the resulting adduct. The catalyst may be unsupported or may be supported on a variety of substrates that will be familiar to persons having ordinary skill in the art. Recovery or regeneration procedures that will likewise be familiar to persons having ordinary skill in the art may be employed to enable catalyst reuse. The catalyst type and amount may vary based on a variety of factors including the chosen starting materials, the desired end use for the product and the chosen reaction vessel. Under batch conditions, the catalyst amount may, for example, be about 0.1 to about 20 wt-% or about 1 to about 5 wt-% catalyst per 100 parts by weight of reactive starting materials. Under continuous conditions, the starting material space velocities typically will be adjusted to provide the desired degree of catalyst exposure, product yield and selectivity.

The reaction temperature for forming the adduct of the first and second compounds may for, example, be maintained below about 150° C., below about 120° C., below about 80° C., or below about 60° C. Typically the reaction temperature will be above about 20° C. (e.g., ambient temperature or above), although any suitable temperature in which the reaction occurs to a desired extent may be used. In some embodiments, the reaction used to form the adduct of the first and second compounds may be performed at ambient temperature. Any suitable pressure may be employed in conducting the reaction, including, for example, ambient pressure or elevated pressure.

By way of example, when the first compound is diacetylbenzene and the second compound is acetylene, the aforementioned reaction of the first and second compounds (e.g., when conducted at room temperature) is believed to result in the below adduct:

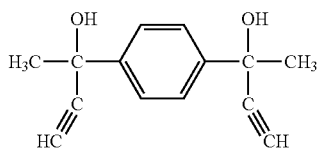

The subsequent carbonation reaction used to form a PCC compound from the adduct of the first and second compounds can likewise be conducted under any suitable reaction conditions, including at any suitable temperature and pressure (e.g., any of the reaction temperatures referenced above). In some embodiments, the carbonation reaction is conducted at a temperature of about 80° C. Any suitable reaction parameters (e.g., temperature, pressure, reaction time, etc) can be used. Some examples of suitable reaction conditions include a temperature of about 80° C. and a pressure of about 5 bars and a temperature of about 120° C. and a pressure of about 2 bars.

The resulting PCC compounds may be used as is or purified prior to use. In general, the use of a purification method may depend on factors including the chosen reaction scheme, yield, byproducts and the form (e.g., solid or liquid) in which the product is obtained. Exemplary purification methods will be familiar to persons having ordinary skill in the art and include washing with solvent, solvent extraction, flotation, filtration, centrifugation, evaporation, crystallization, recrystallization, fractionation, electrolysis, sublimation, adsorption, distillation and biological methods including fermentation, microbes and enzymes.

The disclosed PCC compounds provide useful raw or starting materials for the preparation of a variety of polymers (e.g., homopolymers and copolymers). The polymers may be branched or linear. The PCC compound may be reacted with any suitable extender or combination of extenders to achieve a polymer having the desired molecular weight and structure. For example, the PCC compound (e.g., compounds of Formulas I or IV) may be reacted with a polyfunctional extender compound having two or more functional groups that are reactive with cyclocarbonate functional groups, with difunctional extender compounds being preferred. (By "difunctional" it is meant that the extender only includes two functional groups that are reactive with cyclocarbonate groups under the desired reaction conditions.) Examples of suitable polyfunctional extender compounds include polyacids, polyols (including, e.g., polyhydric phenols), polyamines (e.g., dicyclohexyl amine, diethylene triamine, neopentylamine, etc.), polyamidoamines (e.g., adducts of amino terminal dimer fatty acid and ethylene diamine, hexamethylene diamine, etc.), compounds containing a phenol and amino groups such as hydroxyphenol amines (e.g., catechol amine, dopamine, tyramine, octopamine, etc.), and variants and mixtures thereof. Preferred such extenders include diphenols, diamines, and diamidoamines. Diols or diacids may also be preferable in some embodiments.

In some embodiments, the extenders may include any of the cyclic groups described herein. For example, in some embodiments, the extenders preferably include one or more aryl or heteroaryl groups, with substituted or unsubstituted phenylene groups being preferred examples of such groups. In other embodiments, the extenders may include one or more saturated or unsaturated cycloaliphatic groups such as, for example, any of those previously described herein.

Suitable polyhydric phenols (e.g., dihydric phenols) include hindered diphenols (for example, 4,4'-methylenebis (2,6-dimethylphenol)) as described in U.S. application Ser. No. 13/570,743 (Niederst et al. '743, now published as US 2013/0316109); nonsubstituted diphenols that are appreciably non-estrogenic (for example, 4,4'-(1,4-phenylenebis (propane-2,2-diyl))diphenol and 2,2'methylenebis(phenol)) as also described in Niederst et al. '743; diphenols such as those described (for example, the bis-4-hydroxybenzoate of cyclohexanedimethanol) in U.S. Pat. No. 8,129,495 B2 (Evans et al. '495), and the dihydric phenol compounds of Formula E shown below:

Formula E

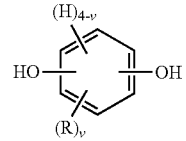

wherein:
 each R, if present, is preferably independently an atom or group preferably having at atomic weight of at least 15 Daltons;
 v is 0 to 4, and
 two or more R groups can optionally join to form one or more cyclic groups.

Exemplary dihydric phenol compounds of Formula E include catechol and substituted catechols (e.g., 3-methylcatechol, 4-methylcatechol, 4-tert-butyl catechol, and the like); hydroquinone and substituted hydroquinones (e.g., methylhydroquinone, 2,5-dimethylhydroquinone, trimethylhydroquinone, tetramethylhydroquinone, ethylhydroquinone, 2,5-diethylhydroquinone, triethylhydroquinone, tetraethylhydroquinone, tert-butylhydroquinone, 2,5-di-tert-butyl hydroquinone, and the like); resorcinol and substituted resorcinols (e.g., 2-methylresorcinol, 4-methyl resorcinol, 2,5-dimethylresorcinol, 4-ethylresorcinol, 4-butylresorcinol, 4,6-di-tert-butylresorcinol, 2,4,6-tri-tert-butylresorcinol, and the like); and variants and mixtures thereof. Additional suitable dihydric phenol compounds are disclosed in U.S. Patent Application Publication No. US 2013/0206756 A1 (Niederst et al. '756) and International Application No. WO 2013/119686 A1 (Niederst et al. '686).

If desired, one or more comonomers or co-oligomers may also be included with the reactants used to generate the disclosed polymers. The comonomers or co-oligomers may for example be included in an initial reaction mixture of PCC compound and extender(s) or may be post-reacted with the resulting oligomer or polymer. In presently preferred embodiments, a comonomer or co-oligomer are not utilized to produce the disclosed polymers.

Molecular weight advancement may be enhanced by the use of a suitable catalyst in an amount sufficient to facilitate the desired reaction Examples of suitable catalysts may include phosphines, aliphatic or cycloaliphatic amines, and combinations thereof.

The type of polymer backbone included in the disclosed polymer will vary depending upon the extender or extenders chosen and any other co-reactants (e.g., comonomers), if any, used in making the polymer. Thus, for example, the polymer may be a polyether, a polycarbamate, a polyester, or a copolymer of any of these polymer types.

In preferred embodiments, the disclosed polymer includes a plurality of segments derived from the PCC compound described herein (e.g., the PCC compound of Formulas I or IV), which are preferably dispersed throughout a backbone of the polymer, more preferably a polyether backbone. In preferred embodiments, the segments derived from the PCC compound (hereinafter "PCC segments") constitute a substantial portion of the overall mass of the polymer. Typically, the PCC segments constitute at least 10 weight percent ("wt-%"), preferably at least 30 wt-%, more preferably at least 40 wt-%, even more preferably at least 50 wt-%, and optimally at least 55 wt-% of the polymer.

In some embodiments, the weight percent of the PCC segments in the polymer may be below the amounts recited above, and can even be substantially below. By way of example, the concentration of PCC segments may be outside the ranges recited above if the polymer includes large molecular weight additional components such as may occur, for example, when the polymer is a copolymer such as an acrylic-containing copolymer (e.g., an acrylic-polyether copolymer formed by grafting acrylic onto a polyether polymer of the present disclosure).

The disclosed polymers can have any suitable glass transition temperature ("Tg"). In certain preferred embodiments, the coating composition disclosed herein is suitable for use in forming a food-contact packaging coating. In order to exhibit a suitable balance of coating properties for use as a food-contact packaging coating, including suitable corrosion resistance when in prolonged contact with packaged food or beverage products which may be of a corrosive nature, in some embodiments, the disclosed polymer preferably has a Tg of at least 40° C., more preferably at least 50° C., and even more preferably at least 60° C. or at least 70° C. In preferred such embodiments, the Tg is less than 150° C., more preferably less than 130° C., and even more preferably less than 110° C. Tg can be measured via differential scanning calorimetry ("DSC"). In preferred embodiments, the polymer is a polyether polymer exhibiting a Tg pursuant to the aforementioned Tg values.

While not intending to be bound by any theory, it is believed that it is important the polymer exhibit a Tg such as that described above in applications where the coating composition will be in contact with food or beverage products during retort processing at high temperature (e.g., at temperatures at or above about 100° C. and sometimes accompanied by pressures in excess of atmospheric pressure), and particularly when retort processing food or beverage products that are more chemically aggressive in nature. It is contemplated that, in some embodiments, such as, for example, where the coating composition is intended for use as an exterior varnish on a food or beverage container (or non-packaging coating end uses), the Tg of the polymer may be less than that described above (e.g., as low as about 30° C.) and the coating composition may still exhibit a suitable balance of properties in the end use.

When the Tg of a polymer is referenced herein in the context of a coating composition including the polymer or an article coated with such a coating composition, the indicated Tg value for the polymer refers to the Tg of the polymer prior to any cure of a coating composition including the polymer.

An example of a useful DSC test procedure for determining Tg is described as follows. Samples for DSC testing are prepared by first applying the liquid resin composition onto aluminum sheet panels. The panels are then baked in a Fisher Isotemp electric oven for 20 minutes at 300° F. (149° C.) to remove volatile materials. After cooling to room temperature, the samples are scraped from the panels, weighed into standard sample pans and analyzed using the standard DSC heat-cool-heat method. The samples are equilibrated at −60° C., then heated at 20° C. per minute to 200° C., cooled to −60° C., and then heated again at 20° C. per minute to 200° C. Glass transitions are calculated from the thermogram of the last heat cycle. The glass transition is measured at the inflection point of the transition.

While not intending to be bound by any theory, it is believed that the inclusion of a sufficient number of aryl and/or heteroaryl groups (typically phenylene groups) in the disclosed binder polymers is an important factor for achieving suitable coating performance for food-contact packaging coatings, especially when the product to be packaged is a so called "hard-to-hold" food or beverage product. Sauerkraut is an example of a hard-to-hold product. In preferred embodiments, aryl and/or heteroaryl groups constitute at least 25 wt-%, more preferably at least 30 wt-%, and even more preferably at least 35 wt-% or at least 45 wt-% of the polymer, based on the total weight of aryl and heteroaryl groups in the polymer relative to the weight of the polymer. The upper concentration of aryl/heteroaryl groups is not particularly limited, but preferably the amount of such groups is configured such that the Tg of the polymer is within the Tg ranges previously discussed. The total amount of aryl and/or heteroaryl groups in the polymer will typically constitute less than about 80 wt-%, more typically less than 75 wt-%, and even more typically less than about 70 wt-% or less than 60 wt-% of the polymer. The total amount of aryl and/or heteroaryl groups in the polymer can be determined based on the weight of aryl- or heteroaryl-containing monomer incorporated into the polymer and the weight fraction of such monomer that constitutes aryl or heteroaryl groups. In embodiments where the polymer is, for example, a polyether copolymer (e.g., a polyether-acrylic copolymer), the weight fraction of aryl or heteroaryl groups in the polyether polymer portion(s) of the copolymer will generally be as described above, although the weight fraction relative to the total weight of the copolymer may be less.

Preferred aryl or heteroaryl groups include less than 20 carbon atoms, more preferably less than 11 carbon atoms, and even more preferably less than 8 carbon atoms. The aryl or heteroaryl groups preferably have at least 4 carbon atoms, more preferably at least 5 carbon atoms, and even more preferably at least 6 carbon atoms. Substituted or unsubstituted phenylene groups are preferred aryl or heteroaryl groups. Thus, in preferred embodiments, the polymer includes an amount of phenylene groups pursuant to the amounts recited above.

The disclosed upgraded molecular weight polymers may be applied to a variety of substrates as liquid or powder-based coating compositions. Liquid coating compositions (typically including the polymer and a liquid carrier) may be preferred for many end uses, especially for use on heat-sensitive substrates or for substrates where an especially thin coating is desired. Exemplary liquid carriers include water, organic solvents, and mixtures of liquid carriers. Exemplary organic solvents include glycol ethers, alcohols, aromatic or aliphatic hydrocarbons, dibasic esters, ketones, esters, and the like. Preferably, such carriers are selected to provide a dispersion or solution of the polymer with which additional additives may be combined to provide a final coating formulation.

In one embodiment, the disclosed liquid coating compositions are solvent-based systems that include no more than a de minimus amount of water (e.g., less than 2 wt-% of water). The disclosed solvent-based liquid coating compositions may, for example, contain at least 20 wt-% non-volatile components (viz., "solids"), and more preferably at least 25 wt-% non-volatile components. The disclosed solvent-based liquid coating compositions may also, for example, contain no greater than 50 wt-% non-volatile components or no greater than 40 wt-% non-volatile components.

In one embodiment, the coating composition is a water-based composition preferably having at least 15 wt-% non-volatile components. In one embodiment, the coating composition is a water-based composition preferably having no greater than 50 wt-% non-volatile components, and more preferably no greater than 40 wt-% non-volatile components. Water-based coating systems of the present invention may optionally include one or more organic solvents, which will typically be selected to be miscible in water. The liquid carrier system of water-based coating compositions will typically include at least 50 wt-% of water, more typically at least 75 wt-% of water, and in some embodiments more than 90 wt-% or 95 wt-% of water. Any suitable means may be used to render the polymer of the present invention miscible in water. For example, the polymer may include a suitable amount of salt groups such as ionic or cationic salt groups to render the polymer miscible in water (or groups capable of forming such salt groups). Neutralized acid or base groups are preferred salt groups.

The disclosed polymers may serve as a binder polymer in the disclosed coating compositions. The binder polymer amount may vary widely depending on a variety of considerations including the method of application, the presence of other film-forming materials, whether the coating composition is a water-based or solvent-based system, and so on. For liquid-based coating compositions, the binder polymer will typically constitute at least 10 wt-%, more typically at least 30 wt-%, and even more typically at least 50 wt-% of the coating composition, based on the total weight of resin solids in the coating composition. For such liquid-based coating compositions, the binder polymer will typically constitute less than about 90 wt-%, more typically less than about 80 wt-%, and even more typically less than about 70 wt-% of the coating composition, based on the total weight of resin solids in the coating composition.

Preferred coating compositions are substantially free, more preferably essentially free, and more preferably completely free of one or more or all of mobile: BPA, bisphenol S ("BPS"), bisphenol F, bisphenol A diglycidyl ether (BADGE), bisphenol S diglycidyl ether, and bisphenol F diglycidyl ether. Preferred coating compositions are also substantially free, more preferably essentially free, and more preferably completely free of one or more or all of bound: BPA, bisphenol S, bisphenol F, bisphenol A diglycidyl ether (BADGE), bisphenol S diglycidyl ether, and bisphenol F diglycidyl ether.

In preferred embodiments, the coating composition is at least substantially free, and more preferably completely free, of mobile or bound polyhydric phenols having estrogenic agonist activity greater than or equal to that of 4,4'-(propane-2,2-diyl)diphenol. Even more preferably, the coating composition is at least substantially free, and more preferably completely free, of mobile or bound polyhydric phenols having estrogenic agonist activity (e.g., in the MCF-7 assay) greater than or equal to that of BPS. Even more preferably, the coating composition is at least substantially free, and more preferably completely free, of mobile or bound polyhydric phenols having estrogenic agonist activity (e.g., in the MCF-7 assay) greater than that of 4,4'-(propane-2,2-diyl)bis(2,6-dibromophenol). Optimally, the coating composition is at least substantially free, and more preferably completely free, of mobile or bound polyhydric phenols having estrogenic agonist activity (e.g., in the MCF-7 assay) greater than about that of 2,2-bis(4-hydroxyphenyl)propanoic acid).

In some embodiments, the coating composition is substantially free of one or both of glycidyl ether compounds or aromatic glycidyl ether compounds, more preferably essentially free of one or both of these compounds, and even more preferably completely free of one or both of these compounds.

In some embodiments, the coating composition is "PVC-free." That is, in some embodiments, the coating composition preferably contains less than 2 wt-% of vinyl chloride materials, more preferably less than 0.5 wt-% of vinyl chloride materials, and even more preferably less than 1 ppm of vinyl chloride materials. In some embodiments, the coating composition preferably includes less than 2 wt-% of halogenated compounds (e.g., compounds containing a fluorine atom (F), chlorine atom (Cl), or bromine atom (Br)), more preferably less than 0.5 wt-% of halogenated compounds, and even more preferably less than 1 ppm of halogenated compounds.

When the disclosed coating compositions include polymers having suitable reactive groups (for example, amino groups, phenyl hydroxyl groups, acid or anhydride groups, or ethylenically unsaturated groups), the coating composition preferably also is formulated using one or more optional curing agents (for example, crosslinking resins, sometimes referred to as "crosslinkers"). The choice of a particular crosslinker typically depends on the particular product being formulated. For example, some coating compositions are highly colored (e.g., gold-colored coatings). These coatings may typically be formulated using crosslinkers that themselves tend to have a yellowish color. In contrast, white coatings are generally formulated using non-yellow or non-yellowing crosslinkers, or only a small amount of a yellow or yellowing crosslinker.

Preferred curing agents are substantially free of mobile BPA and mobile BADGE and more preferably completely free of bound BPA and bound BADGE. Suitable examples of curing agents include hydroxyl-reactive curing resins such as phenoplasts, aminoplast, blocked or unblocked isocyanates, or mixtures thereof.

Exemplary phenoplast resins include the condensation products of aldehydes with phenols. Formaldehyde and acetaldehyde are preferred aldehydes. Various phenols can be employed including phenol, cresol, p-phenylphenol, p-tert-butylphenol, p-tert-amylphenol and cyclopentylphenol. The phenoplast resins may be of either the resole type or the novolac type, or a mixture thereof.

Exemplary aminoplast resins are the condensation products of aldehydes such as formaldehyde, acetaldehyde, crotonaldehyde, and benzaldehyde with amino- or amido-group-containing substances such as urea, melamine, and benzoguanamine. Examples of suitable aminoplast crosslinking resins include, without limitation, benzoguanamine-formaldehyde resins, melamine-formaldehyde resins, etherified melamine-formaldehyde, and urea-formaldehyde resins.

Exemplary other generally suitable curing agents include blocked or non-blocked aliphatic, cycloaliphatic or aromatic di-, tri-, or poly-valent isocyanates, such as hexamethylene diisocyanate, cyclohexyl-1,4-diisocyanate, and the like. Further non-limiting examples of generally suitable blocked isocyanates include isomers of isophorone diisocyanate, dicyclohexylmethane diisocyanate, toluene diisocyanate, diphenylmethane diisocyanate, phenylene diisocyanate, tetramethyl xylene diisocyanate, xylylene diisocyanate, and mixtures thereof. In some embodiments, blocked isocyanates having an Mn of at least about 300, more preferably at least about 650, and even more preferably at least about 1,000 may be used. Polymeric blocked isocyanates are useful in certain embodiments. Exemplary polymeric blocked isocyanates include a biuret or isocyanurate of a diisocyanate, a trifunctional "trimer", or a mixture thereof. Commercially available blocked polymeric isocyanates include TRIXENE™ BI 7951, TRIXENE BI 7984, TRIXENE BI 7963, TRIXENE BI 7981 (available from Baxenden Chemicals, Ltd., Acerington, Lancashire, England); DESMODUR™ BL 3175A, DESMODUR BL3272, DESMODUR BL3370, DESMODUR BL 3475, DESMODUR BL 4265, DESMODUR PL 340, DESMODUR VP LS 2078, DESMODUR VP LS 2117, and DESMODUR VP LS 2352 (available from Bayer Corp., Pittsburgh, Pa., USA); and combinations thereof. Exemplary trimers include a trimerization product prepared from on average three diisocyanate molecules or a trimer prepared from on average three moles of diisocyanate (e.g., HMDI) reacted with one mole of another compound such as, for example, a triol (e.g., trimethylolpropane).

The level of curing agent (viz., crosslinker) used will typically depend on the type of curing agent, the time and temperature of the bake, and the molecular weight of the binder polymer. If used, the crosslinker is typically present in an amount of up to 50 wt-%, preferably up to 30 wt-%, and more preferably up to 15 wt-%, based on the total weight of the resin solids in the coating composition. If used, a crosslinker is preferably present in an amount of at least 0.1 wt-%, more preferably at least 1 wt-%, and even more preferably at least 1.5 wt-%, based upon the total resin solids weight.

The disclosed coating compositions may also include other optional polymers that do not adversely affect the coating composition or a cured coating thereof. Such optional polymers are typically included as a nonreactive filler material, although they may be included as a reactive crosslinker, or to provide other desired properties. Such optional nonreactive filler polymers include, for example, polyesters, acrylics, polyamides, and polyethers. Alternatively, such additional polymeric materials or monomers may be reactive with other components of the composition (e.g., an acid-functional or unsaturated polymer). If desired, reactive polymers may be incorporated into the disclosed compositions, for example to provide additional functionality for various purposes, including crosslinking or to assist in dispersing the disclosed upgraded molecular weight polymers into water. Examples of such reactive polymers include, for example, functionalized polyesters, acrylics, polyamides, and polyethers. Preferred optional polymers are substantially free of mobile BPA and mobile BADGE, and more preferably completely free of such compounds.

Another preferred optional ingredient is a catalyst to increase the rate of cure. Examples of catalysts, include, but are not limited to, strong acids including phosphoric acid, dodecylbenzene sulfonic acid (DDBSA, available as CYCAT 600 from Cytec), methane sulfonic acid (MSA), p-toluene sulfonic acid (pTSA), dinonylnaphthalene disulfonic acid (DNNDSA), and triflic acid; quaternary ammonium compounds; phosphorous compounds, and tin, titanium, and zinc compounds. Specific examples include, but are not limited to, a tetraalkyl ammonium halide, a tetraalkyl or tetraaryl phosphonium iodide or acetate, tin octoate, zinc octoate, triphenylphosphine, and similar catalysts known to persons having ordinary skill in the art. If used, a catalyst is preferably present in an amount of at least 0.01 wt-%, and more preferably at least 0.1 wt-%, based on the weight of nonvolatile material in the coating composition. If used, a catalyst is preferably present in an amount of no greater than 3 wt-%, and more preferably no greater than 1 wt-%, based on the weight of nonvolatile material in the coating composition.

Another useful optional ingredient is a lubricant (e.g., a wax), which facilitates manufacture of fabricated metal articles (e.g., container closures and food or beverage can ends) by imparting lubricity to sheets of coated metal substrate. Non-limiting examples of suitable lubricants include, for example, natural waxes such as Carnauba wax or lanolin wax, polytetrafluoroethane (PTFE) and polyethylene-type lubricants. If used, a lubricant is preferably present in the coating composition in an amount of at least 0.1 wt-%, and preferably no greater than 2 wt-%, and more preferably no greater than 1 wt-%, based on the total weight of nonvolatile material in the coating composition.

Another useful optional ingredient is a pigment, such as titanium dioxide. If used, a pigment is present in the disclosed coating composition in an amount of no greater than 70 wt-%, more preferably no greater than 50 wt-%, and even more preferably no greater than 40 wt-%, based on the total weight of solids in the coating composition.

Surfactants may optionally be added to the disclosed coating composition to aid in flow and wetting of a substrate Examples of surfactants include, but are not limited to, nonylphenol polyethers and salts and similar surfactants known to persons having ordinary skill in the art. If used, a surfactant is preferably present in an amount of at least 0.01 wt-%, and more preferably at least 0.1 wt-%, based on the weight of resin solids. If used, a surfactant is preferably present in an amount no greater than 10 wt-%, and more preferably no greater than 5 wt-%, based on the weight of resin solids.

The disclosed coating compositions may also include other optional ingredients that do not adversely affect the coating composition or cured coating thereof. Such optional ingredients are typically included in a coating composition to enhance composition esthetics; to facilitate manufacturing, processing, handling, or application of the composition; or to further improve a particular functional property of a coating composition or a cured coating thereof. For example, the disclosed coating compositions may optionally include fillers other than those already mentioned, dyes, colorants, toners, coalescents, extenders, anticorrosion agents, flow control agents, thixotropic agents, dispersing agents, antioxidants, oxygen-scavenging materials, adhesion promoters, light stabilizers, and mixtures thereof, as required to provide desired film properties. Each optional ingredient is preferably included in a sufficient amount to serve its intended purpose, but not in such an amount to adversely affect a coating composition or a cured coating thereof.

The disclosed coating compositions may be present as a layer of a mono-layer coating system or as one or more layers of a multi-layer coating system. The coating composition can be used as a primer coat, an intermediate coat, a top coat, or a combination thereof. The coating thickness of a particular layer and of the overall coating system will vary depending upon the coating material used, the substrate, the coating application method, and the end use for the coated article. Mono-layer or multi-layer coil coating systems including one or more layers formed from the disclosed coating composition may have any suitable overall coating thickness, but, e.g. for packaging coating applications such as food or beverage container coatings, will typically have an overall average dry coating thickness of from about 2 to about 60 micrometers and more typically from about 3 to about 12 micrometers.

The disclosed coating compositions may be applied to a substrate (typically a metal substrate) either prior to, or after, the substrate is formed into an article such as, for example, a food or beverage container or a portion thereof. In one embodiment, a method of forming food or beverage cans is provided that includes: applying a coating composition described herein to a metal substrate (e.g., applying the composition to the metal substrate in the form of a planar coil or sheet), hardening the composition, and forming (e.g., via stamping) the substrate into a packaging container or a portion thereof (e.g., a food or beverage can or a portion thereof). For example, two-piece or three-piece cans or portions thereof such as riveted beverage can ends with a cured coating of the disclosed coating composition on a surface thereof can be formed in such a method. In another embodiment, a method of forming food or beverage cans is provided that includes: forming (e.g., via stamping) a metal substrate into a packaging container or a portion thereof (e.g., a food or beverage can or a portion thereof), applying a coating composition described herein to the inside, outside or both inside and outside portions of such packaging container or a portion thereof, and hardening the composition. For example, the coating composition may be spray applied to an interior surface of a preformed food or beverage can (e.g., as typically occurs with "two-piece" food or beverage cans). The disclosed upgraded molecular weight polymers are especially desirable for use on the inside or interior portion of such food or beverage containers, and for other applications involving a food or beverage contact surface or involving a metal substrate. Exemplary such applications include two-piece drawn food cans, three-piece food cans, food can ends, drawn and ironed food or beverage cans, beverage can ends, easy open can ends, twist-off closure lids, and the like.

Suitable metal substrates include, for example, steel or aluminum. The metal substrate used in forming rigid food or beverage cans, or portions thereof, typically has a thickness in the range of about 0.005 inches to about 0.025 inches. Electro tinplated steel, cold-rolled steel, and aluminum are commonly used as metal substrates for food or beverage cans, or portions thereof. In embodiments in which a metal foil substrate is employed in forming, e.g., a packaging article, the thickness of the metal foil substrate may be even thinner that that described above.

The coating composition can be applied to a substrate using any suitable procedure such as spray coating, roll coating, coil coating, curtain coating, immersion coating, meniscus coating, kiss coating, blade coating, knife coating, dip coating, slot coating, slide coating, and the like, as well as other types of premetered coating. Where the coating is used to coat metal sheets or coils, the coating can be applied by roll coating. After applying the coating composition onto a substrate, the composition can be cured using a variety of processes, including, for example, oven baking by either conventional or convectional methods, or any other method that provides an elevated temperature suitable for curing the coating. The curing process may be performed in either discrete or combined steps. For example, substrates can be dried at ambient temperature to leave the coating compositions in a largely uncrosslinked state. The coated substrates can then be heated to fully cure the compositions. In certain instances, the disclosed coating compositions may be dried and cured in one step.

The cure conditions will vary depending upon the method of application and the intended end use. The curing process may be performed at any suitable temperature, including, for example, oven temperatures in the range of from about 100° C. to about 300° C., and more typically from about 177° C. to about 250° C. If a metal coil is the substrate to be coated, curing of the applied coating composition may be conducted, for example, by heating the coated metal substrate over a suitable time period to a peak metal temperature ("PMT") of preferably greater than about 177° C. More preferably, the coated metal coil is heated for a suitable time period (e.g., about 5 to 900 seconds) to a PMT of at least about 218° C.

It is contemplated that coating compositions of the present invention may also have utility in end uses other than packaging coating end uses. For example, other coating end uses may include industrial coatings, marine coatings (e.g., for ship hulls), coatings for storage tanks (e.g., metal or concrete), architectural coatings (e.g., on cladding, metal roofing, ceilings, garage doors, etc.), coatings for gardening tools and equipment, toy coatings, automotive coatings, metal furniture coatings, coil coatings for household appliances, floor coatings, and the like. It is also contemplated that the coating composition may have utility in cosmetic packaging or medical packaging coating end uses, and as a drug-contact coating in particular (e.g., as an interior coating of a metered dose inhaler can—commonly referred to as an "MDI" container). It is also contemplated that the coating composition may have utility in coating applications in which the coated substrate will contact bodily fluids such as, e.g., as an interior coating of a blood vial.

The following examples are offered to aid in understanding of the present invention and are not to be construed as limiting the scope thereof. Unless otherwise indicated, all parts and percentages are by weight.

Example 1

Adduct Formation 24 grams (0.15 moles) of para-diacetylbenzene and 350 grams of liquid ammonia were added to a stainless steel autoclave. The mixture was saturated with acetylene at room temperature to reach 4 to 5 bars of pressure. 2 grams KOH (0.018 moles) were added and the reaction mixture was left overnight at room temperature. After release of the gas pressure, the reaction mixture was diluted with ice water (200 milliliters) and neutralized with hydrochloric acid (36%). The resulting yellow oil was gradually crystallized, filtered, washed and dried. This product was identified by nuclear magnetic resonance (NMR) as the addition product of diacetylbenzene and acetylene. The yield was 70% (calculated on diacetyl benzene) and the melting point was determined to 141-143° C. The structure of the adduct product was determined to be as follows:

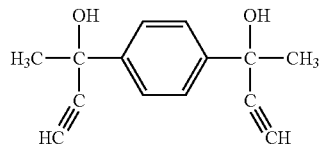 [SMILES: C#CC(C)(O)c1ccc(C(C)(O)C#C)cc1]

Example 2

Conversion of the Adduct into a PCC Compound

The adduct of Example 1 (1.071 grams, 5 millimoles) was mixed with 0.043 grams 1,3-bis(2,6-disopropylphenyl)-imidazolidinium chloride (CAS 258278-25-0) and 0.017 grams silver acetate in 6.061 milliliters (mL) dichloromethane. The reaction mixture was stirred at 80° C. under 25 atm carbon dioxide pressure during 24 hours. After dissolution of the resulting reaction product in 10 mL dichloroethane and filtration, the product was crystallized from a mixture of dichloromethane and diethyl ether. This product was identified via NMR as the below depicted dicyclocarbonate species. The yield was 71% (calculated on the Example 1 adduct) and the melting point was of the material was 133 to 135° C.

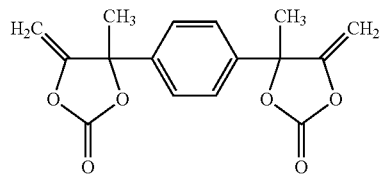

Example 3

Polyether Polymer Synthesis

It is expected that a polyether polymer can be produced via condensation of the dicyclocarbonate compound of Example 2 with a dihydric phenol (e.g., hydroquinone) in presence of a basic catalyst (e.g., triethylamine or 1, 5-Diazabicyclo (4.3.0) Non-5-Ene) using reaction conditions and equipment that will familiar to those skilled in the art. The expected polyether polymer product is depicted below

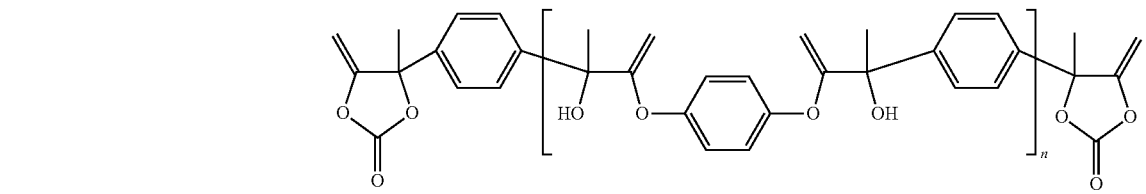

U.S. Provisional Application No. 61/984,535 filed on Apr. 25, 2014 by Gibanel et al. and entitled "Polycyclocarbonate Compounds and Polymers and Compositions Formed Therefrom" (Attorney Docket No. 06-2259-0100), and the PCT application filed on even date herewith and claiming priority to U.S. Provisional Application No. 61/984,535, are each incorporated herein by reference.

Having thus described preferred embodiments of the present invention, those of skill in the art will readily appreciate that the teachings found herein may be applied to yet other embodiments within the scope of the claims hereto attached. The complete disclosure of all listed patents, patent documents and publications (including material safety data sheets, technical data sheets and product brochures for the raw materials and ingredients used in the Examples) are incorporated herein by reference as if individually incorporated.

What is claimed is:

1. A polymer formed from a reaction of a polycyclocarbonate compound and an extender having at least two functional groups reactive with a cyclocarbonate group, wherein the polycyclocarbonate compound has at least two carbonate-containing rings and one or more further cyclic groups, the polycyclocarbonate is formed by a method comprising reacting reactants including: a first compound including at least two carbonyl functional groups; a second compound having a carbon-carbon triple bond; and
    carbon dioxide; and wherein the polymer comprises a polyether polymer that comprises a reaction product of the polycyclocarbonate compound with a diphenol compound.

2. The polymer of claim 1, wherein the polycyclocarbonate compound is an ethylenically unsaturated polycyclocarbonate compound.

3. The polymer of claim 1, wherein the polymer has a number average molecular weight of at least 2,000, a glass transition temperature of at least 30° C., and aryl or heteroaryl groups constitute at least 25 weight percent of the polymer.

4. The polymer of claim 2, wherein the ethylenically unsaturated polycyclocarbonate compound is an ethylenically unsaturated dicyclocarbonate compound.

5. The polymer of claim 1, wherein the polycyclocarbonate compound has the structure of Formula I

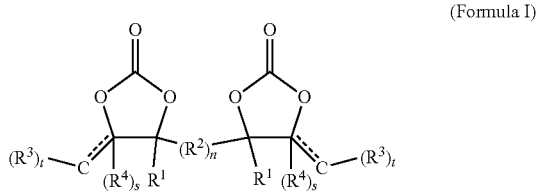

(Formula I)

wherein
each $R^1$ is independently hydrogen or an organic group;
$R^2$, if present, is a divalent organic group;
each $R^3$ is independently hydrogen or an organic group;
each $R^4$ is independently hydrogen or an organic group;
n is 0 or 1;
each s is independently 0 or 1, and wherein when s is 0 a double bond is located between the carbon atom to which $R^3$ is attached and the adjacent carbon atom of the carbonate ring, and wherein when s is 1 a single bond is present between these two carbon atoms;
each t is independently 1, 2, or 3; and
two or more of $R^1$, $R^2$, or $R^4$ of each ring can optionally join to form a cyclic group.

6. The polymer of claim 2, wherein n is 1 and $R^2$ includes one or more cyclic groups.

7. A coating composition including the polymer of claim 1, wherein the coating composition is a liquid coating composition.

8. An ethylenically unsaturated polymer comprising the condensation reaction product of an extender having at least two functional groups reactive with a cyclocarbonate group and an ethylenically unsaturated polycyclocarbonate compound including at least one cyclic group in addition to the cyclocarbonate groups.

9. The polymer of claim 8, wherein the ethylenically unsaturated polycyclocarbonate compound has a structure of Formula II

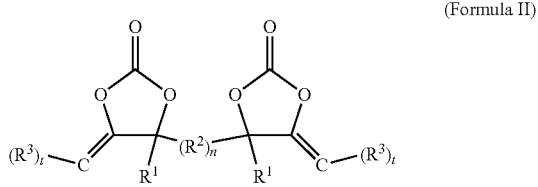

(Formula II)

wherein
each $R^1$ is independently hydrogen or organic group;
$R^2$, if present, is a divalent organic group;
each $R^3$ is independently hydrogen or organic group;
n is 0 or 1;
each t is independently 1 or 2; and
two or more of $R^1$ or $R^2$ of each ring can optionally join to form a cyclic group.

10. The polymer of claim 8, wherein the ethylenically unsaturated polycyclocarbonate compound has a molecular weight of less than 1,500.

11. The Polymer of claim 8, wherein the extender includes polyacids, polyols, polyamines, polyamidoamines, compounds containing a phenol and amino groups, or mixtures thereof.

12. The polymer of claim 11, wherein the extender is a dihydric phenol.

13. The polymer of claim 12, wherein the dihydric phenol has a structure of Formula III

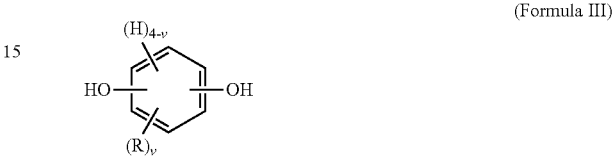

(Formula III)

wherein
each R, if present, is independently hydrogen or group having an atomic weight of at least 15 Daltons;
v is 0 to 4; and
two or more R groups can optionally join to form one or more cyclic groups.

14. The polymer of claim 8, wherein the polymer has a number average molecular weight of at least 2,000, a glass transition temperature of at least 30° C., and aryl or heteroaryl groups constitute at least 25 weight percent of the polymer.

15. A polymer comprising a polyether, polyester, or copolymer thereof formed from a reaction of a polycyclocarbonate compound and an extender having at least two functional groups reactive with a cyclocarbonate group, wherein the polycyclocarbonate compound has at least two carbonate-containing rings and one or more further cyclic groups, the polycyclocarbonate is formed by a method comprising reacting reactants including: a first compound including at least two carbonyl functional groups; a second compound having a carbon-carbon triple bond; and
carbon dioxide; and wherein the at least one further cyclic group is selected from a monocyclic, polycyclic, or cycloaliphatic group that is saturated or unsaturated.

16. The polymer of claim 15, wherein the extender is selected from polyacids, polyols, compounds containing a phenol and amino groups, or mixtures thereof.

17. The ethylenically unsaturated polymer of claim 8, wherein the ethylenically unsaturated polymer is a polyether, a polycarbamate, a polyester, or a copolymer thereof.

18. The ethylenically unsaturated polymer of claim 8, wherein the at least one cyclic group is selected from a monocyclic, polycyclic, or cycloaliphatic group that is saturated or unsaturated.

19. The polymer of claim 15, wherein the polymer has a number average molecular weight of at least 2,000, a glass transition temperature of at least 30° C., and aryl or heteroaryl groups constitute at least 25 weight percent of the polymer.

20. The polymer of claim 15, wherein the polycyclocarbonate compound is an ethylenically unsaturated polycyclocarbonate compound.

* * * * *